United States Patent
Guan et al.

(10) Patent No.: US 7,141,215 B2
(45) Date of Patent: Nov. 28, 2006

(54) AROMATIC EVAPORATOR

(75) Inventors: Jin-Chin Guan, Taipei Hsien (TW); Ming-Tarng Yeh, Taipei Hsien (TW)

(73) Assignee: Hsu-Yang Technologies Co., Ltd., Taipei Hsien (TW)

( * ) Notice: Subject to any disclaimer, the term of this patent is extended or adjusted under 35 U.S.C. 154(b) by 728 days.

(21) Appl. No.: 10/228,938

(22) Filed: Aug. 28, 2002

(65) Prior Publication Data

US 2004/0042935 A1    Mar. 4, 2004

(51) Int. Cl.
   *A62B 7/08* (2006.01)
   *B05B 1/24* (2006.01)

(52) U.S. Cl. .......................... 422/125; 239/54; 239/55; 239/75; 239/136; 422/123

(58) Field of Classification Search ................ 422/123, 422/125; 239/54, 55, 75, 136
   See application file for complete search history.

(56) References Cited

U.S. PATENT DOCUMENTS 5,178,839 A * 1/1993 Spector ...................... 422/123
5,394,506 A * 2/1995 Stein et al. .................. 392/395
6,249,645 B1 * 6/2001 Smith .......................... 392/403
6,278,840 B1 * 8/2001 Basaganas Millan ....... 392/390
6,603,924 B1 * 8/2003 Brown et al. ............... 392/390
6,672,129 B1 * 1/2004 Frederickson et al. ....... 73/1.06
6,852,278 B1 * 2/2005 Richards ........................ 422/4

* cited by examiner

Primary Examiner—Krisanne Jastrzab
(74) Attorney, Agent, or Firm—Troxell Law Office, PLLC

(57) ABSTRACT

The present invention is an aromatic evaporator consisting of a base, a heater, a heat conduction aluminum plate, a constant temperature controller, a plug, a ceramic carriers and a cover. The plug sets inside the base to deliver D.C. power; the heater converts the electricity from the plug into heat; the heat conduction aluminum plate adhered to the heater directly evens the heat; the constant temperature controller contains the electric conduction switch and the memory alloy plate connected with the heat conduction aluminum. When the memory alloy plate is straight, the electric conduction switch is switched off and stops the heater from heating. When the temperature reduces, the memory alloy plate is curved by external force and switches on the electric conduction switch, making the heater reheat. The memory alloy plate of the constant temperature controller controls the heater to heat intermittently, making the heater heat at constant temperature.

3 Claims, 4 Drawing Sheets

AROMATIC EVAPORATOR

BACKGROUND OF THE INVENTION

Traditional aromatic evaporators for automobiles and indoor use contain two types: one is placed at the vent that blows away the aroma and the other is placed directly in the automobile or indoors to disperse the aroma. The aroma dispersed from these two types of aromatic evaporators usually comes from low-volatility and unstable synthetic attar and causes allergy to human bodies. Moreover, the dispersion of aroma by constantly heating and evaporating might fresh people's spirits and help people stay sober; however, its persistent heating method for a long time might turn out thickening or overheating the aroma and deteriorates the attar, putting people under the weather. Besides, the deposition of the evaporated attar contaminates everything inside the automobile.

For automobile aromatic evaporators, a need exists to replace the whole aromatic evaporator or the whole attar bottle when running up the attar, which is cost-consuming and against economic benefits. Therefore, the necessity for improvement does exist.

SUMMARY OF THE INVENTION

The main objective for the present invention is to provide an aromatic evaporator with a constant temperature controller that controls the heater to conduct heat intermittently by switching on and off an electric conduction switch with a memory alloy plate, preventing the attar from deteriorating and attached to the automobile, the indoors or human bodies and causing contamination and damage because of overheating, thus disperses aroma securely and prolongs the running time of the attar.

Another objective for the present invention is to provide an aromatic evaporator with a ceramic carrier that absorbs and stores up attar. With the attar extracted from natural plants as the material for evaporation, the phytoncide aroma dispersed from the attar through the heated ceramic carrier freshens people's mind and comforts people's body, without running the risk of causing damage under long-term usage.

Another objective for the present invention is to provide an aromatic evaporator with a capillary ceramic carrier that soaks attar for storage and disperses the phytoncide aroma of the attar under heating. Whenever the ceramic carrier runs out of attar, it could be replenished by re-absorbing the attar. Due to the possibility of long-term usage for the ceramic carrier that absorbs and stores up attar, the necessity of replacement is eliminated and the present invention is more cost-saving and provides more economic benefits.

In the following, the embodiment illustrated is used to describe the detailed structural characteristics and operation action for the present invention.

DETAILED DESCRIPTION OF THE INVENTION

Figure 1:
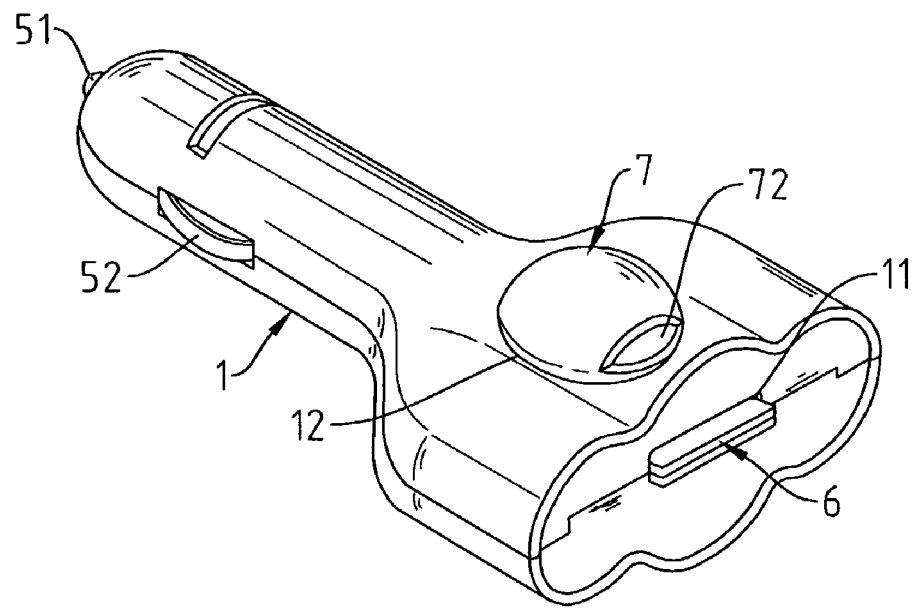
FIG. 1 is a diagram about the three-dimensional appearance for the present invention.
Figure 2:
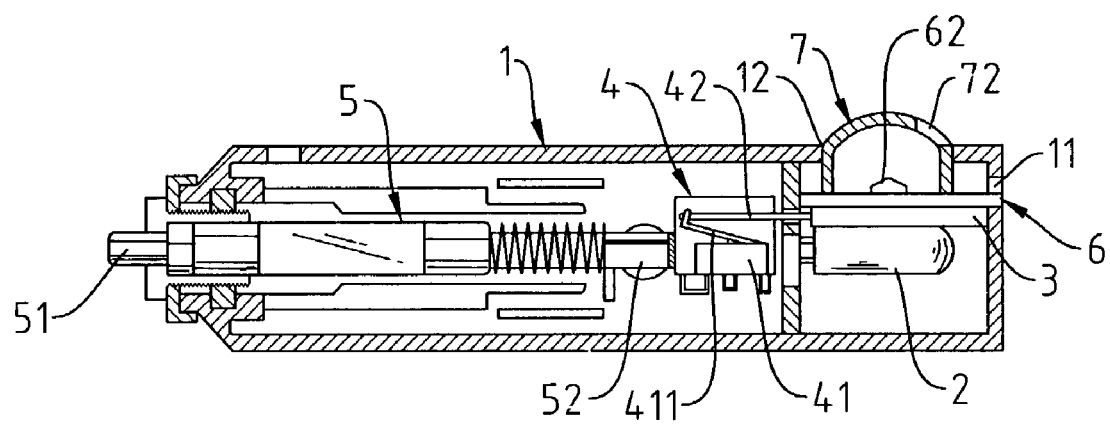
FIG. 2 is a diagram about the cross-section for the present invention.
Figure 3:
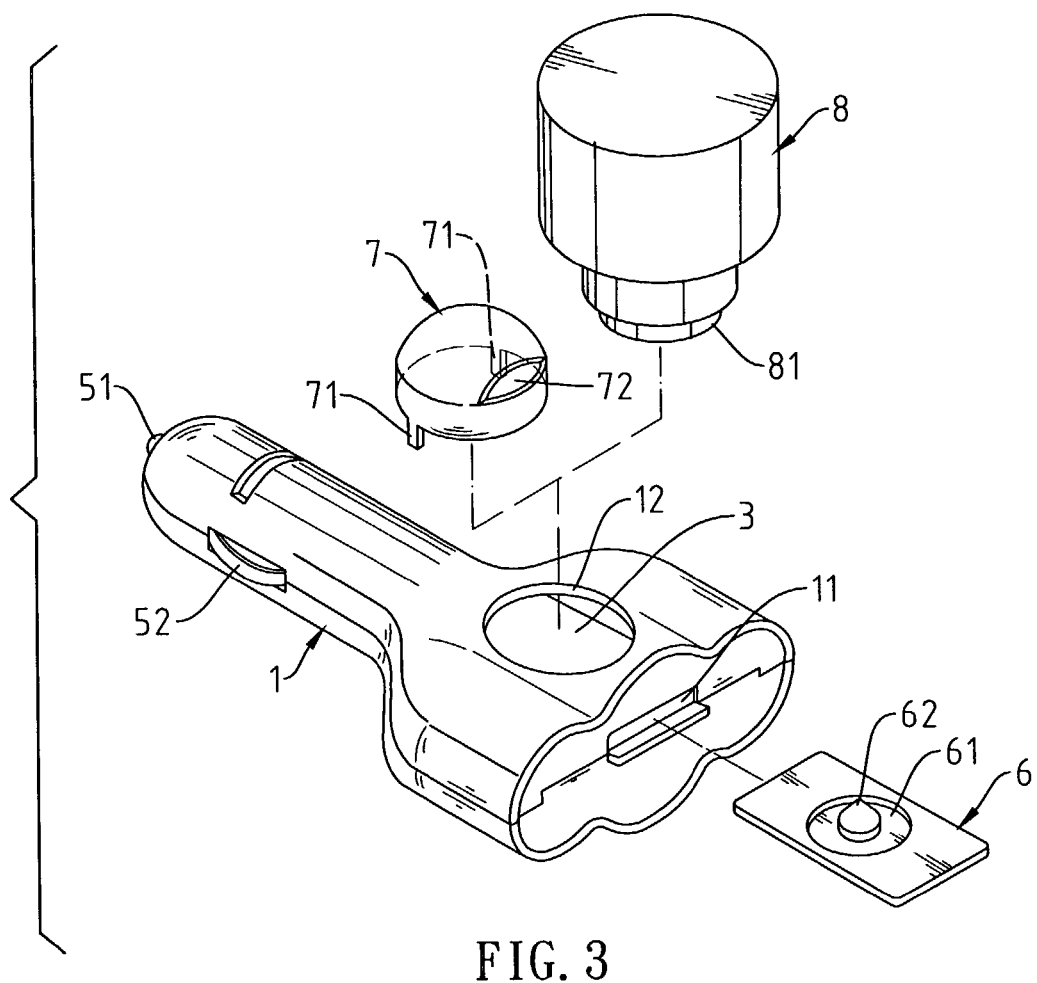
FIG. 3 is a diagram about the decomposition of the assemblies for the present invention.

Please refer to FIG. 1 to FIG. 3. The aromatic evaporator for the present invention consists of one base 1, one heater 2, one heat conduction aluminum plate 3, one constant temperature controller 4, one plug 5, one ceramic carrier 6 and one cover 7.

Inside the base 1 there is a plug 5 with a positive contact 51 and a negative contact 52 on one end and the other end is connected to the heater 2, delivering D.C. power to the heater 2 that converts electricity into heat. The heat conduction aluminum plate 3 adhered above the heater 2 evens the heat when being heated by the heater 2.

Figure 7:
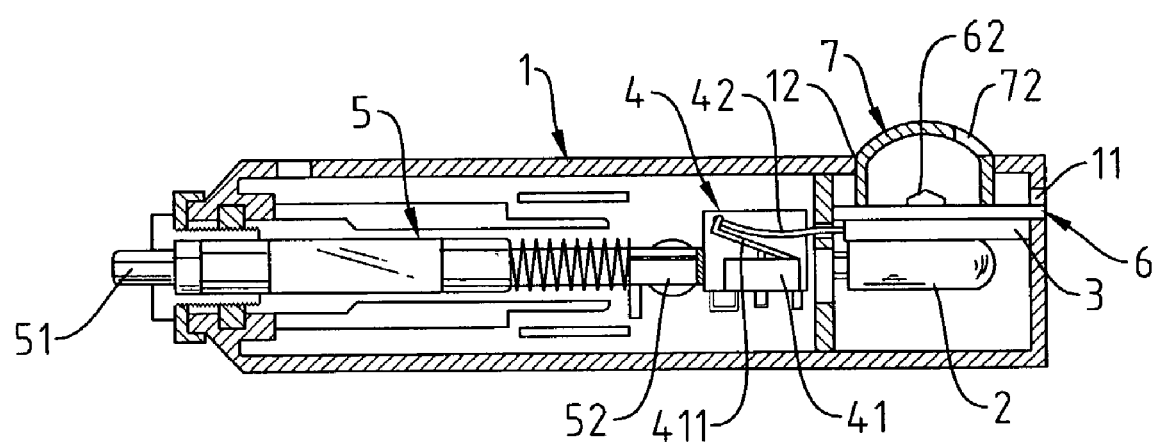
FIG. 7 is a diagram about the memory alloy plate of the constant temperature controller for that present invention that switches on the circuit of the electric conduction switch when cooling down.

The constant temperature controller 4 containing one electric conduction switch 41 and one memory alloy plate 42 is set at the middle of the base 1. The electric conduction switch 41 is connected with the positive contact 51 and the negative contact 52 of the plug 5, acting as the contact for switching on or off the heater 2. The memory alloy plate 42 is connected to the heat conduction aluminum 3 on one end and to the flexible contact plate 411 of the electric conduction switch 41 on the other end. When the memory alloy plate 42 receives certain degree of heat from the heat conduction aluminum 3, it becomes straight as it used to be and switches off the circuit to the positive contact 51 of the plug 5 connected to the electric conduction switch 41, turning it into a broken circuit (as shown in FIG. 2). During a broken circuit, if the temperature of the heater 2, the heat conduction aluminum plate 3 and the memory alloy plate 42 drops gradually, the flexibility of the flexible contact plate 411 forces the memory alloy plate to curve (as shown in FIG. 7), thus switches on the circuit to the positive contact 51 of the plug 5 connected to the electric conduction switch 41 and start to heat again. The memory alloy plate 42 that changes shape in accordance with the variation of the temperature controls the power for the heater 2, allowing the heater 2 to stop heating under high temperature and start reheating under low temperature. By repeatedly switching on and of the heating of the heater 2, the heater 2 is able to heat at a constant temperature and is more secure.

Figure 4:
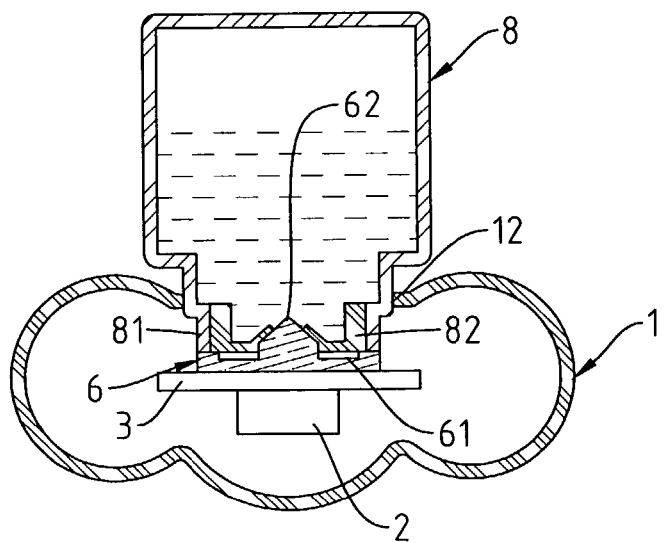
FIG. 4 is a diagram about the combinative cross-section of the attar bottle and the ceramic carrier for the present invention.
Figure 5:
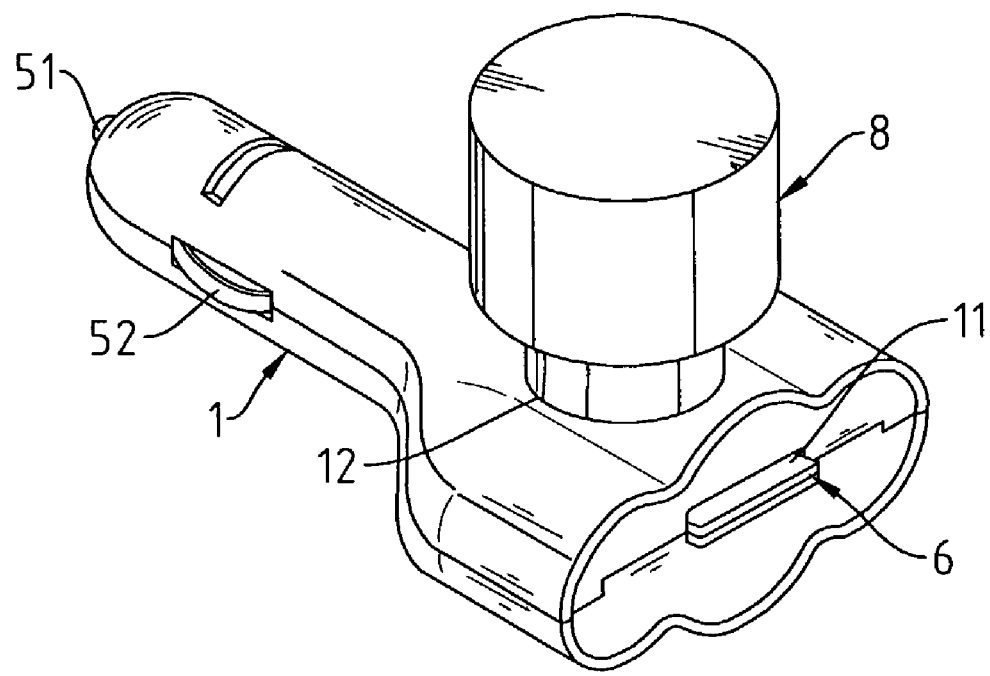
FIG. 5 is a diagram about the operation of the attar bottle for the present invention.

The above ceramic carrier 6 is a sinter containing aluminum, sodium, magnesium, calcium and silicon with tiny capillaries between each granular on the surface. When the attar is poured on the surface, it gets adhered to the capillaries and stored inside the body of the ceramic carrier 6. At the center of the surface of the ceramic carrier 6 there is a dent circular fillister 61 with a cone 62 protruding upward in the middle. The cone 62 allows the attar bottle 8 with its mouth 81 sealed to insert. Even the sealing membrane 82 is pierced through, the attar bottle 8 upside down does not leak out the attar because the cone 82 absorbs the attar that spread across the interior of the ceramic carrier 6 while secures the attar bottle placed upside down (as shown in FIG. 4 and FIG. 5).

Figure 6:
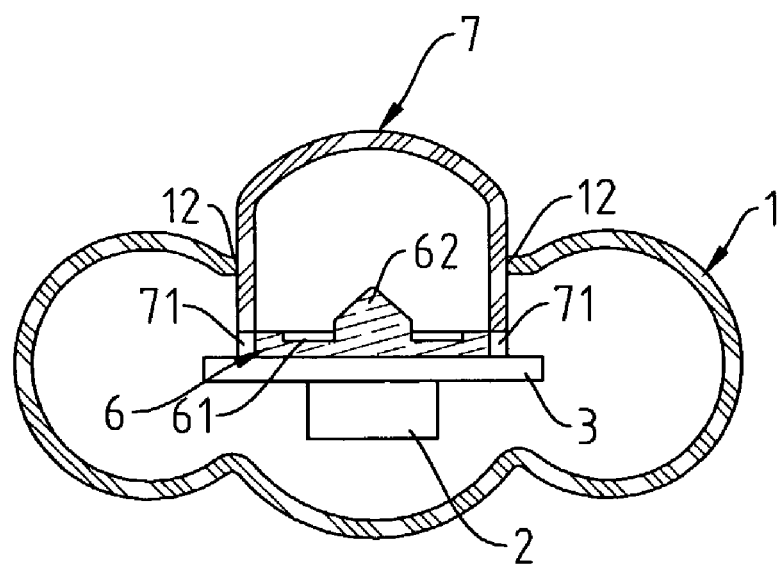
FIG. 6 is a diagram about the heating of the ceramic carrier soaked with attar for the present invention.

A socket 11 is set on the rear of the base 1 to which the ceramic carrier 6 is inserted. Above the socket 11 there is a trough 12 allowing for the covering of the cover 7 or the insertion of the attar bottle 8. The cover 7 placed on the trough 12 has a clip stick 71 stretching downward on each side. The distance between the two clip sticks 71 equal to the width of the ceramic carrier 6 so as to clips and fastens the ceramic carrier 6 inside the base 1 when the ceramic carrier 6 is inserted into the socket 11 (as shown in FIG. 6). What's more, a window 72 is set on the edge of the cover 7 for exhausting the air from inside out.

During the application of the aromatic evaporator for the present invention, the attar bottle 8 could be detached from the ceramic carrier 6 already soaked with attar. Then, the attar stored inside the ceramic carrier 6 is warmed up by the heat transmitted through the heat conduction aluminum plate 3 heated by the heater 2 to release the phytoncide, so as to help people stay sober and comfort people's body and mind, without running the risk of damaging human bodies under long-term usage. When the attar stored inside the ceramic carrier 6 runs up, replenishing the attar inside the ceramic carrier 6 by placing the attar bottle 8 upside down on the ceramic carrier 6 is allowed so as to use the ceramic carrier 6 as an attar storage media without any replacement needed, thus makes it more cost-saving and provides more economic benefits.

Furthermore, when the memory alloy plate 42 receives certain degree of heat transmitted from the heat conduction aluminum plate 3, it becomes straight as it used be and switches off the circuit of the positive contact 51 on the plug 5 connected to the electric conduction switch 4, forcing the heater 2 to stop heating temporarily. When the temperature of the memory alloy plate 42 reduces, the elasticity of the flexible contact plate 411 forces the memory alloy plate 42 to curve, switching on the circuit of the positive contact 51 on the plug 5 connected to the electric conduction switch 4 and forces the heater 2 to reheat. Thus, the memory alloy plate 42 that changes its shape with the variation of the temperature controls the circuit to the heater for intermittent on and off, providing the whole device with more secure constant-temperature heating.

What is claimed is:

1. An aromatic evaporator comprising: one base, one heater, one heat conduction aluminum plate, one constant temperature controller, one plug, one ceramic carrier and one cover, wherein a positive and negative contact are set on one side of said plug inside said base to provide D.C. power with another end connected to said heater changing electricity into heat in a middle of said base sits said constant temperature controller controlling an electric conduction circuit of said heater, said heat conduction aluminum plate is located on a top of said heater for heat conduction, and said ceramic carrier having an attar is placed above said heat conduction aluminum plate to release an aroma through heating, said cover is placed on top of a trough of said base exhausting the aroma, wherein said constant temperature controller contains one electric conduction switch and one memory alloy plate, wherein said electric conduction switch is connected with said positive and said negative contact of said plug for electric conduction while said memory allow plate is connected to said heat conduction aluminum plate on a first end and to one flexible contact plate of said electric conduction switch on a second end, said memory allow plate becomes straight when receiving a certain degree of heat transmitted from said heat conduction aluminum plate so as to control displacement of said flexible contact plate, wherein said memory alloy plate straightens under a higher temperature to stop said flexible contact plate from conducting electricity and curves under a lower temperature to force said flexible contact plate to resume conducting, thus said memory alloy plate switches on and off said electric conduction circuit of said heater intermittently and providing a secure constant-temperature from said heater.

2. The aromatic evaporator of claim 1, wherein said ceramic carrier is a sinter containing aluminum, sodium, magnesium, calcium and silicon with capillaries that absorb attar being poured above and stored in said ceramic carrier.

3. The aromatic evaporator of claim 1, wherein said ceramic carrier has a circular recess located on a top thereof and a cone protruding upwardly from a center of said recess, said cone pierces through a sealing cover of an attar bottle placed upside down above said ceramic carrier, preventing attar from leaking out and enabling said attar to be absorbed by said cone and spreading across an inside of said ceramic carrier.

* * * * *